US00PP10460P

United States Patent [19]

Khanizadeh et al.

[11] Patent Number: Plant 10,460

[45] Date of Patent: Jun. 23, 1998

[54] 'JOLIETTE' STRAWBERRY

[76] Inventors: Shahrokh Khanizadeh, 64 Apple Hill, Baie d'Urfé, Québec, Canada, H9X 3H4; Deborah Buszard, 128 Strathearn Ave., Montreal West, Quebec, Canada, H4X 1X9

[21] Appl. No.: 636,073

[22] Filed: Apr. 22, 1996

[51] Int. Cl.[6] ..... A01H 5/00

[52] U.S. Cl. ..... Plt./48

[58] Field of Search ..... Plt./48

[56] References Cited

PUBLICATIONS (UPOCEOM Citation), CA BPR 96–816 for 'Joliette' published Aug. 29, 1996.

Khanizadeh, S., et al. (1996) "'Joliette' Strawberry" HortScience 31(6) Oct. p. 1036, 1996.

*Primary Examiner*—James R. Feyrer

*Attorney, Agent, or Firm*—Leydig, Voit & Mayer, Ltd.

[57] ABSTRACT

A Nordic-type strawberry variety named 'Joliette' combines the characteristics of adaptability to heavy soil conditions, and resistance to low winter temperatures (<−30° C.), water stress, the herbicide terbacil, and leaf diseases, and its high yield of firm, glossy red skin fruit at maturity with light red flesh with a very small white, raised neck.

4 Drawing Sheets

BACKGROUND OF THE INVENTION

The invention relates to a new and distinctive cultivar of strawberry plant named 'Joliette'. This cultivar belongs to the genus *Fragaria* (×*ananassa Duch.*), whose fruits are juicy, edible and usually red, and is cultivated for culinary purposes.

Species of strawberry plants vary in color, size, shape, acidity, and other commercially important and botanically significant characteristics. Strawberries frequently bear flowers and fruit simultaneously, and fruit tends to ripen randomly on the stems.

ORIGIN OF THE VARIETY

The new cultivar of the present invention 'Joliette' was tested as SJ89288-2, progeny of a cross made in 1989 between 'Jewel' and SJ85189 (Redchief×Surecrop) by S. Khanizadeh. 'Jewel' is a relatively new commercial cultivar in eastern central Canada and is noted for large, firm, glossy fruit with good flavor and resistance to leaf spot (*M. fragariae*) and post harvest fruit rot. SJ85189 war retained in our breeding program because of its very large fruit, adaptation to heavy soil, and resistance to low winter temperatures (<−30° C.), water stress, the herbicide terbacil, and leaf diseases (leaf spot, leaf scorch and powdery mildew). The strawberry was created at Agriculture and Agrifood Canada Research Station, St. Jean-sur-Richelieu, Quebec, Canada and was asexually reproduced, by runners, at the same location.

DESCRIPTION OF THE FIGURES

The accompanying photographs illustrate the color and other features of the new cultivar showing it in various stages of fruit maturation.

FIG. 1 is a close-up view of fruits of the variety in different stages of maturity.

FIG. 2 is a close-up view of foliage of the variety.

FIG. 3 is a close-up view of foliage of the variety.

FIG. 4 is a comparison of 'Joliette' fruit with Kent fruit.

DESCRIPTION OF THE VARIETY

Figure 5:
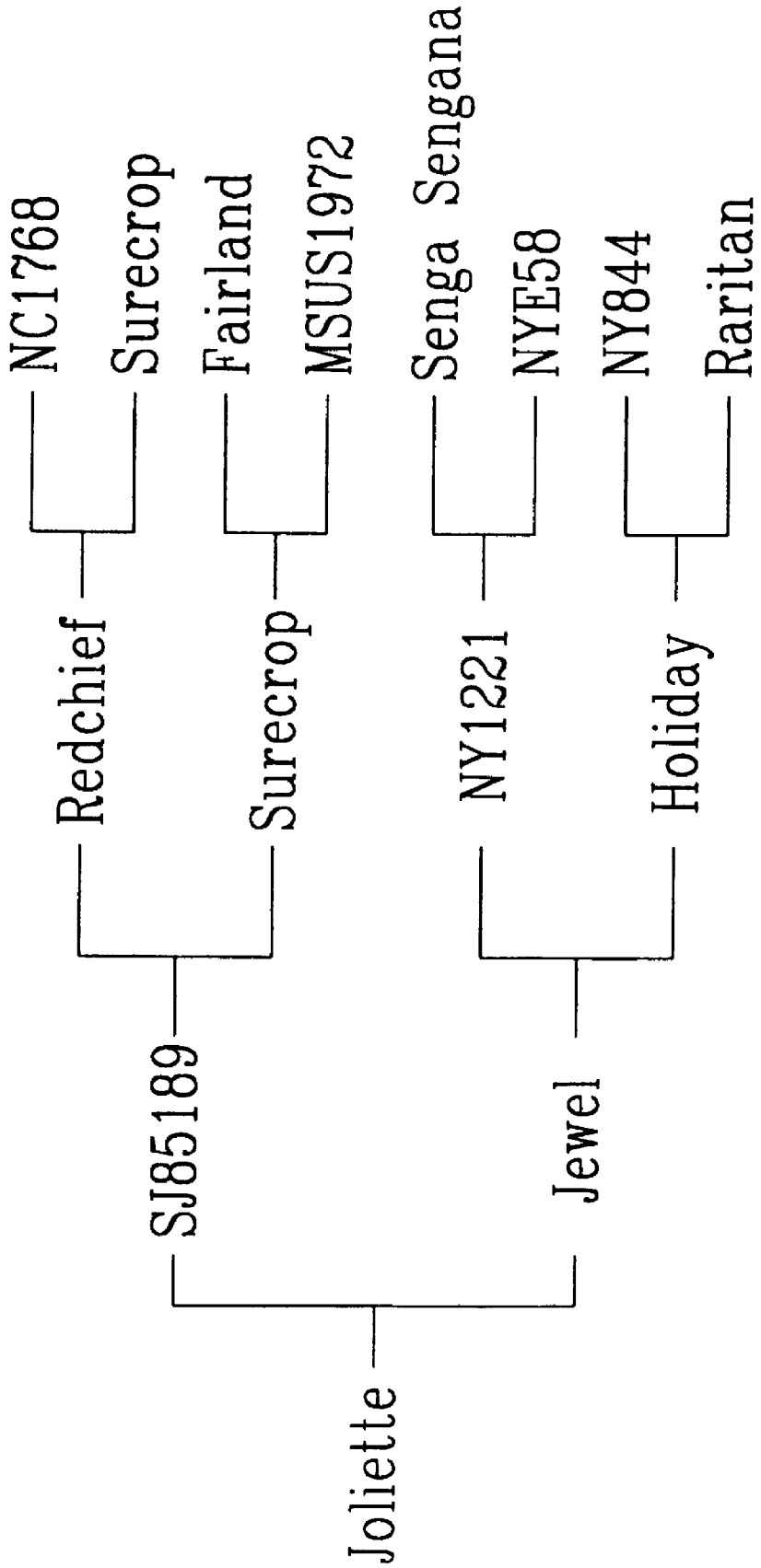
FIG. 5 is a pedigree of the 'Joliette' strawberry.

'Joliette' is a short day June bearing strawberry cultivar (*Fragaria×ananassa Duch.*) released through collaboration of Agriculture and Agri-Food Canada and McGill University. 'Joliette' has high yields of large, moderately firm fruit and it is resistant to leaf spot (*Mycosphaerella fragariae Tul.*) and to six North American eastern (NAE) races of red stele (*Phytophthora fragariae* Hickman). It is recommended for fresh market and pick your own.

The name 'Joliette' refers to a town located on the l'Assomption river in southern Quebec. It is one of the major strawberry growing areas renowned for its sandy soils, which are perfectly suited for irrigated production of nursery plants and fruit.

'Joliette' plants are vigorous, medium in size, with 5 to 7 inflorescnece, i.e. flower stalks, per plant and can tolerate winter temperatures below −25° C. (with 10 cm straw mulch cover). The propensity of 'Joliette' is similar to that of 'Kent' in terms of runner coloration, thickness and inflorescence, although 'Joliette' has thcker stolons and more even fruit surfaces. The plant is strong in vigour, globose in habit and of medium density. Sufficient pollen is produced to allow for monoculture of the plant without supplemental pollination from other plants. The anthocyanin coloration of the stipules (as observed on one-year-old plants in autumn) is medium. Petioles, which are of medium pubescence and the hairs of which are posed upwards, are long with three leaflets and have medium pubescence. Leaflets are flat, medium size, dark green, obovate with about 21 sharp serrations (leaf length=84 mm (compared to 77.8 mm for 'Kent'); leaf width=74.5 mm (compared to 66.8 mm for 'Kent'); n=5 for both measurements). The terminal leaflets are longer than broad and have obtuse bases and margins with acutely shaped teeth. The leaves of 'Joliette' strawberry are dark green in color. They are slightly concave in cross section and weakly blistering. Plants do not have a dense appearance. Inflorescence are held erect during flowering, becoming semi-erect as the fruit mature. Inflorescences generally have 10 to 15 flowers (flower petal length=9.25 mm (compaed to 8.55 mm for 'Kent'); flower petal width=7.75 mm (compared to 6.5 mm for 'Kent'); n=5 fir both measurements).

'Joliette' produces a medium number of stolons, which have medium pubescence. The stolons of 'Joliette' are thick in comparison to the stolons of 'Kent', which are medium in thickness, and medium in anthocyanin coloration. The flowers of 'Joliette' are positioned level with the foliage and are medium in size. The diameter of the calyx is smaller than that of the corolla. The flower petals are broader than long and are touching to overlapping.

The fruiting truss of 'Joliette' is medium in length and the attitude at first picking is semi-erect. The fruit length to width ratio is longer than broad. The fruit size is large and predominantly conical in shape. There is a moderate difference in shape between the primary and secondary fruits for 'Joliette,' whereas 'Kent' shows less of a difference. Evenness of the fruit surface is very strong for 'Juliette,' while it is medium for 'Kent.' The fruit has even, red skin color and an absent or very narrow band without achenes. The achenes are below the surface of the fruit. The fruits appear above the leaves at first and, as the fruits form, they lower within the leaves. The calyx of 'Joliette' is level with the fruit and reflexed, while the calyx of 'Kent' is clasping. The calyx is smaller in than the diameter of the fruit and has medium adherence to the fruit. The fruit flesh of 'Joliette' is firm, whereas that of 'Kent' is medium. The flesh is an even, light red color. The sweetness and acidity of the fruit are medium and the texture of the fruit is fine. Approximately 2 kg of fruit of each cultivar was collected at each harvest and used to evaluate appearance, texture and flavor attributes as described previously. The length of the bearing season is three weeks. Specific measuring systems were used for each attribute. Neck size and calyx form were evaluated using the ranking method. Skin and flesh color, flavor, and firmness were evaluated using the line scale technique. Fruit shape was evaluated using the classification method (fruit length= 32.2 mm (compared to 30.4 mm for 'Kent'); fruit width= 36.2 mm (compared to 34.8 mm for 'Kent'); n=5 for both measurements).

Data collected for all harvests were combined for analysis of variance (ANOVA). Rank and line scaled data were transformed using an arcsin square root percent transformation to make the means and variances independent prior to ANOVA. The ANOVA were done using the General Linear Model Procedure (GLM) of SAS (SAS, 1988). Least significant difference (LSD) was used for mean separation between the cultivars.

Fruit shape changes from globose-conic, similar to 'Kent', to short wedge, similar to 'Bounty', during the harvest, and the calyces are moderately reflexed (Table 1). Fruit are large with a very small white, raised neck. Skin is very glossy red at maturity (R.H.S. red group 43A-43B for fruit prior to maturity and R.H.S. red group 45A-46B for mature fruit), and the flesh is light red throughout R.H.S. red group 43B (Table 1). Fruit flavor is similar to 'Glooscap', 'Oka' and 'Sparkle'. Fruits are moderately firm, similar to 'Kent', and can be decapped easily like 'Chambly'. The fruit of 'Joliette' is solid with no cavity. The fruits keep their integrity after thawing and percent juice lost is similar to other tested cultivars. Plants of 'Joliette' are tolerant of the herbicide terbacil.

| sugar analysis replicate | CODE | SUCROSE (S) | GLUCOSE (G) mg/100 g | FRUCTOSE (F) |
|---|---|---|---|---|
| 1 | SJ89288-2 (Joliette) | 27.662 | 2417.594 | 3123.669 |
| 2 | SJ89288-2 (Joliette) | 27.601 | 2444.250 | 3219.439 |
| 1 | KENT | 12.962 | 2455.852 | 3069.374 |
| 2 | KENT | 12.457 | 2461.450 | 3078.610 |

| sugar analysis replicate | CODE | SGF TOTAL | % SUGAR TOTAL |
|---|---|---|---|
| 1 | SJ89288-2 (Joliette) | 5568.925 | 5.57 |
| 2 | SJ89288-2 (Joliette) | 5691.290 | 5.69 |
| 1 | KENT | 5538.188 | 5.54 |
| 2 | KENT | 5552.516 | 5.55 |

| Acid analysis Replicate | CODE | CITRIC | MALIC | QUINIC | SUCCINIC |
|---|---|---|---|---|---|
| | | mg/100 g | | | |
| 1 | SJ89288-2 | 814.66419 | 377.66078 | 18.219715 | 60.003595 |
| 2 | SJ89288-2 | 879.13576 | 373.54025 | 22.060016 | 78.533657 |
| 1 | KENT | 685.17879 | 419.90493 | 13.71994 | 46.895839 |
| 2 | KENT | 696.87678 | 432.9853 | 19.743898 | 46.243434 |

| Acid analysis Replicate | CODE | TOTAL ACID | % ACID | % SUGAR ACID | % CITRIC |
|---|---|---|---|---|---|
| 1 | SJ89288-2 | 1270.5483 | 1.27 | 5.57 | 0.81 |
| 2 | SJ89288-2 | 1353.2697 | 1.35 | 5.69 | 0.88 |
| 1 | KENT | 1165.6995 | 1.17 | 5.54 | 0.69 |
| 2 | KENT | 1195.8494 | 1.20 | 5.55 | 0.70 |

In addition, the 'Joliette' plant has been fingerprinted and compared to 'Kent.' The results are available from Applicant. Isozyme patterns, however, have not been determined as of yet.

Performance

Similar yield and fruit weight were observed in all tested areas. However the data presented in Table 1 are averaged over six years (1990–1995) for two locations l'Acadie and Lavaltrie. 'Joliette' produced similar yield to 'Honeoye', 'Chambly', 'Oka' and 'Kent' in our trials andhas outyielded 'Bounty', 'Glooscap', 'Redcoat', and 'Sparkle' since 1989 (Table 1). The ripening season of 'Joliette' is similar to 'Glooscap', 'Kent', 'Bounty' and 'Oka' (mid-season). No significant difference was observed among individual fruit weights of 'Joliette', 'Kent', 'Honeoye', and 'Chambly'.

TABLE 1

Comparison of yield, fruit characteristics and ripening season of 'Joliette' vs eight commercially grown strawberry cultivars at Lavaltrie and 1'Acadie, Quebec[z]

| Cultivar | Yield (kg/2 m) | Mean fruit wt (g) | Neck size[y] | Calyx form[y] | Skin color[y] |
|---|---|---|---|---|---|
| Bounty | 3.3 | 9.7 | 3.0 | 3.9 | 3.3 |
| Chambly | 4.5 | 11.9 | 4.0 | 4.7 | 4.0 |
| Glooscap | 3.4 | 9.3 | 3.4 | 4.4 | 3.0 |
| Honeoye | 4.0 | 10.5 | 3.0 | 2.0 | 3.0 |
| Joliette | 4.7 | 12.2 | 3.2 | 3.0 | 2.8 |
| Kent | 3.9 | 11.9 | 3.5 | 3.2 | 2.5 |
| Oka | 5.0 | 8.8 | 2.7 | 2.5 | 3.2 |
| Redcoat | 3.5 | 6.7 | 3.8 | 3.0 | 3.0 |
| Sparkle | 2.6 | 6.6 | 2.4 | 3.4 | 3.0 |
| LSD 5% | 0.8 | 2.6 | 0.3 | 0.2 | 0.2 |

TABLE 1-continued

Comparison of yield, fruit characteristics and ripening season of 'Joliette' vs eight commercially grown strawberry cultivars at Lavaltrie and 1'Acadie, Quebec[z]

| Cultivar | Flesh color[y] | Flavor[y] | Firmness[y] | Ripening season[x] |
|---|---|---|---|---|
| Bounty | 3.0 | 3.8 | 2.0 | L |
| Chambly | 4.0 | 3.6 | 3.8 | EM |
| Glooscap | 3.1 | 3.1 | 2.6 | M |
| Honeoye | 3.0 | 3.0 | 3.0 | EM |
| Joliette | 2.3 | 3.3 | 3.2 | M |
| Kent | 2.5 | 3.0 | 3.3 | M |
| Oka | 2.2 | 3.3 | 3.0 | M |
| Redcoat | 2.8 | 3.0 | 2.8 | EM |
| Sparkle | 2.0 | 3.4 | 2.0 | LM |
| LSD 5% | 0.1 | 0.2 | 0.1 | |

[z]Averaged over six years (1990–1995), minimum of four replicates per year and two locations.
[y]Data were transformed to arcsin prior to analysis of variance (SAS, 1988). Neck size: 1 = none, 5 = long neck; Calyx form: 1 = concave (covered the fruit), 5 = reflexed (away from the fruit); Skin and flesh color: 1 = very pale, 5 = dark red; Flavor: 1 = poor, 5-excellent; Firmness: 1 = very soft, 5 = very firm. For details of ranking see Khanizadeh (1994).
[x]Ripening season: L = late, LM = late-midseason, M = mid-season, EM = early-midseason, E = early.

Disease Resistance

No symptoms of powdery mildew (*Sphaerotheca macularis* Walls ex Fr.), leaf scorch (*Diplocarpon earlina* Ell. and Ev.), leaf blight (*Dendrophoma obscurans* Ell. and Ev.), leaf spot (*Mycosphaerella fragariae* Tul.) have been observed since 1989 in comparison with other standard cultivars like 'Annapolis', 'Bounty', 'Glooscap', 'Honeoye', 'Jewel', 'Kent', 'MicMac', 'Midway', 'Redcoat', 'Sparkle', and 'Veestar'. A greenhouse test was also conducted as described previously (Delhomez et al. 1995) to test the reaction of 'Joliette' toward leaf spot, a common foliar leaf disease in eastern Canada (Craig, 1979; Fall, 1951). No symptoms of leaf spot were observed, beginning eight days after inoculation until the termination of the experiment (23 days) compared to 'Kent', 'Governor Simcoe', 'Oka', 'Bounty', 'Honeoye', and 'Glooscap'.

In 1994–1995, the susceptibility of 'Joliette' to the six NAE races (A-1, A-2, A-3, A-4, A-5, A-6, mixture of A1–A6) of *P. fragariae* was evaluated as described previously (Khanizadeh et al. 1992) in comparison with the resistant cultivar Annapolis and Honeoye (susceptible), sparkle (semi-resistant) and six advanced selections. After 60 days, ten primary root systems per plant were randomly selected to evaluate the presence of red stele and oospores in the root system. No red-steles or oospores were observed in control plants. 'Annapolis' and 'Joliette' were the most resistant genotypes compared to the others genotypes.

Tests and Trials

'Joliette' has been tested extensively at Agriculture and Agri-Food Canada, L'Acadie, Québec since 1989. L'Acadie is located 35 km southeast of Montreal Island, Quebec, (lat. 45° N and 46 m elevation). Climate at L'Acadie is characterized by extreme low temperatures in winter (<−25° C.); cool, wet, humid conditions in spring; and warm, dry, humid conditions (25° C. to 35° C., 70% RH) in summer. It has a clay loam soil with moderate to low drainage and little snow cover during the winter. 'Joliette' has also been tested at McGill University, Ste-Anne de Bellevue (1993–1994), at Ministére de l'Agriculture des Pêcheries et de l'Alimentation du Québec (MAPAQ), Sainte-Foy, Quebec (1992–1994) and at Lavaltrie, Quebec (1991–1993). Ste-Anne de Bellevue is located at the far west of Montreal Island, Quebec, (lat. 45° N and 27 m elevation) close to St. Louis Lake with a sandy clay soil, moderate drainage, and good snow cover. Lavaltrie is located 35 km north of Montreal Island, quebec (lat. 45° N and 30 m elevation), with sandy soil and a continental climate. Sainte Foy, is located in the west of Quebec city the capital of Quebec province (lat. 46° N and 90 m elevation) with sandy clay loam soil and extreme low temperature in winter.

Adaptation and Uses

'Joliette' is recommended for areas which have similar climate and soil type to L'Acadie and Lavaltrie. It performs well in compacted or heavy soils or under water stress. Presently this selection is under evaluation in other Canadian provinces, Germany, Switzerland, Belgium and, Russia.

We claim:

1. A new and distinct cultivar of *Fragaria×ananassa Duch.,* plant named 'Joliette', as herein shown and described, characterized particularly as to uniqueness by the combined characteristics of adaptability to heavy soil conditions, and resistance to low winter temperatures (<−30° C.), water stress, the herbicide terbacil, and leaf diseases, and its high yield of firm, glossy red skin fruit at maturity with light red flesh with a very small white, raised neck.

* * * * *